United States Patent
Kunz et al.

(10) Patent No.: US 10,080,844 B2
(45) Date of Patent: Sep. 25, 2018

(54) SUPPLEMENTARY DEVICE FOR ATTACHMENT TO A DRUG INJECTION DEVICE FOR MONITORING INJECTION DOSES HAVING OCR IMAGING SYSTEM WITH GLARE REDUCTION

(71) Applicant: SANOFI-AVENTIS DEUTSCHLAND GMBH, Frankfurt am Main (DE)

(72) Inventors: Theresa Kunz, Jena (DE); Mario Bock, Hamburg (DE); Gertrud Blei, Jena (DE); Matthew Jones, Warwick Warwickshire (GB); Samuel Steel, Warwickshire (GB); Barry Yates, Warwickshire (GB); Anthony Paul Morris, West Midlands (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/516,866

(22) PCT Filed: Oct. 5, 2015

(86) PCT No.: PCT/EP2015/072906
§ 371 (c)(1),
(2) Date: Apr. 4, 2017

(87) PCT Pub. No.: WO2016/055402
PCT Pub. Date: Apr. 14, 2016

(65) Prior Publication Data
US 2017/0304549 A1    Oct. 26, 2017

(30) Foreign Application Priority Data

Oct. 6, 2014  (EP) .................................... 14187696

(51) Int. Cl.
*G01N 21/55* (2014.01)
*A61M 5/315* (2006.01)
(Continued)

(52) U.S. Cl.
CPC .......... *A61M 5/31525* (2013.01); *A61M 5/24* (2013.01); *G01N 21/55* (2013.01);
(Continued)

(58) Field of Classification Search
CPC ......... G01N 2500/04; G01N 33/57449; G01N 33/564; G01N 33/57419; G01N 33/57423;
(Continued)

(56) References Cited

U.S. PATENT DOCUMENTS 6,110,148 A * 8/2000 Brown ................ A61M 5/1782
222/23
8,773,660 B2 * 7/2014 Pommereau ........ G01F 23/2921
356/343
(Continued)

FOREIGN PATENT DOCUMENTS

WO   WO 2013/120777   8/2013

OTHER PUBLICATIONS

International Search Report and Written Opinion in International Application No. PCT/EP2015/072906, dated Nov. 5, 2015, 12 pages.
(Continued)

*Primary Examiner* — Michael P Stafira
(74) *Attorney, Agent, or Firm* — Fish & Richardson P.C.

(57) ABSTRACT

The subject matter described herein relates to a supplementary device for attachment to an injection device, the supplementary device comprising: a first imaging arrangement and a second imaging arrangement each configured to capture an image of a moveable number sleeve of the injection device
(Continued)

from different respective angles. The supplementary device also comprises a plurality of light sources and a processor arrangement configured to control operation of the first imaging arrangement and the second imaging arrangement and the plurality of light sources and to receive image data from each of the imaging arrangements, wherein the processor arrangement is configured to combine images captured by the first imaging arrangement and the second imaging arrangement into a single image.

15 Claims, 7 Drawing Sheets

(51) Int. Cl.
    *G06T 5/50*     (2006.01)
    *A61M 5/24*     (2006.01)
    *G06K 9/20*     (2006.01)
    *A61M 5/31*     (2006.01)

(52) U.S. Cl.
    CPC ....... *G06T 5/50* (2013.01); *A61M 2005/3126* (2013.01); *A61M 2205/3306* (2013.01); *G06K 9/2036* (2013.01)

(58) Field of Classification Search
    CPC ....... G01N 33/57484; G01N 33/57492; G01N 33/6854; G01N 21/3563; G01N 21/3577; G01N 21/359; G01N 21/4738; G01N 21/78
    See application file for complete search history.

(56) References Cited

U.S. PATENT DOCUMENTS

| | | | |
|---|---|---|---|
| 9,435,666 B2* | 9/2016 | Richter | .................. A61M 5/24 |
| 9,561,332 B2* | 2/2017 | Butler | ............... A61M 5/31551 |
| 2008/0165266 A1 | 7/2008 | Jenkins | |
| 2009/0073307 A1 | 3/2009 | Kramer et al. | |
| 2013/0051631 A1 | 2/2013 | Hanna | |
| 2013/0329073 A1 | 12/2013 | Majewicz | |
| 2014/0194826 A1 | 7/2014 | Nielsen et al. | |

OTHER PUBLICATIONS

International Preliminary Report on Patentability in International Application No. PCT/EP2015/072906, dated Apr. 11, 2017, 8 pages.

\* cited by examiner

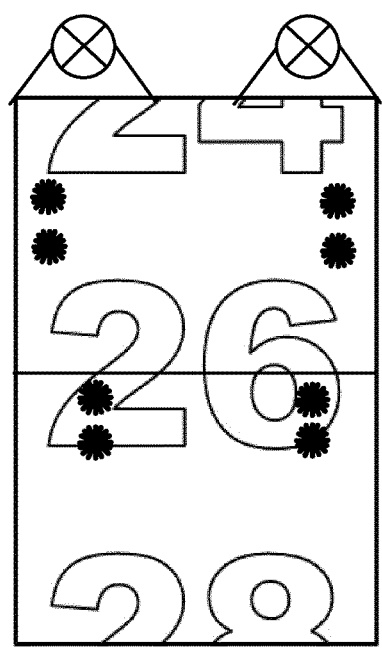 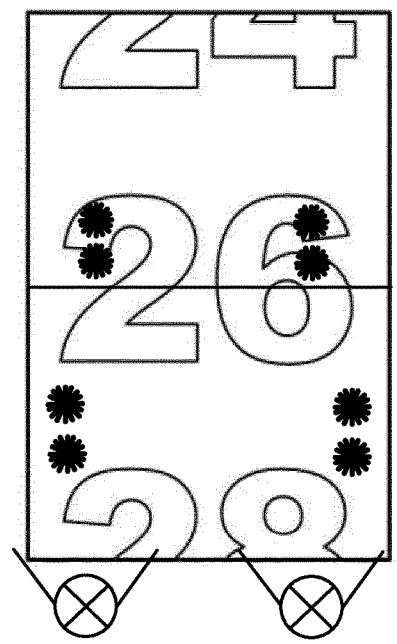
*FIG. 7a*  *FIG. 7b*

SUPPLEMENTARY DEVICE FOR ATTACHMENT TO A DRUG INJECTION DEVICE FOR MONITORING INJECTION DOSES HAVING OCR IMAGING SYSTEM WITH GLARE REDUCTION

CROSS-REFERENCE TO RELATED APPLICATIONS

This application is a U.S. national stage application under 35 USC § 371 of International Application No. PCT/EP2015/072906, filed on Oct. 5, 2015, which claims priority to European Patent Application No. 14187696.1 filed on Oct. 6, 2014, the entire contents of which are incorporated herein by reference.

TECHNICAL FIELD

The present disclosure relates to a supplementary device for attachment to an injection device, and in particular to a supplementary device comprising a processor arrangement configured to activate a plurality of light sources and to combine images captured by a first imaging apparatus and a second imaging apparatus into a single image.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

A first aspect provides a supplementary device for attachment to an injection device, the supplementary device comprising:
  a first imaging arrangement and a second imaging arrangement each configured to capture an image of a moveable number sleeve of the injection device from different respective angles;
  a plurality of light sources; and
  a processor arrangement configured to control operation of the first imaging arrangement and the second imaging arrangement and the plurality of light sources and to receive image data from each of the imaging arrangements,
wherein the processor arrangement is configured to combine images captured by the first imaging arrangement and the second imaging arrangement into a single image.

The processor arrangement may be further configured to activate the plurality of light sources sequentially and to combine images captured by the first imaging arrangement and the second imaging arrangement under different illumination conditions into a single image. Alternatively, the processor arrangement may be configured to activate all of the plurality of light sources simultaneously.

The processor may be configured to divide a field of view of each of the first and second imaging arrangements into a plurality of areas and to associate each of the areas with a respective illumination condition.

The processor arrangement may be configured to combine multiple images captured by the first imaging arrangement and the second imaging arrangement into a single image by being configured to combine an image of a first area of the plurality of areas captured by the first imaging arrangement under a first illumination condition with an image of a second area of the plurality of areas captured by the second imaging arrangement under a second illumination condition.

The supplementary device may comprise four light sources grouped into first and second pairs and the processor arrangement may be configured to activate the plurality of light sources sequentially by being configured to activate the first pair of light sources followed by the second pair of light sources.

The processor may be further configured to:
  control the first imaging arrangement to capture a first image of the number sleeve when the first pair of light sources are activated; and
  control the second imaging arrangement to capture a second image of the number sleeve when the second pair of light sources are activated.

The processor may be configured to divide the field of view of the first and second imaging arrangements into first and second halves. The processor may be configured to keep the first half of the first image and discard the second half of the first image and to keep the second half of the second image and discard the first half of the second image. The processor arrangement may be configured to combine images captured by the first imaging arrangement and the second imaging arrangement into a single image by being configured to combine the first half of the first image and the second half of the second image into a single image.

Each illumination source, when activated, may result in one or more reflections from a transparent window of the injection device being visible in a field of view of each of the first and second imaging arrangements.

A second aspect provides a system comprising a supplementary device according to the first aspect and an injection device comprising a moveable number sleeve and being configured to have the supplementary device of the first aspect attached thereto.

A third aspect provides a method of operating a supplementary device for attachment to an injection device, the supplementary device having a first imaging arrangement and a second imaging arrangement each configured to capture an image of a moveable number sleeve of the injection device from different respective angles, a plurality of light sources and a processor arrangement, the method comprising:
  controlling operation of the first imaging arrangement, the second imaging arrangement and the plurality of light sources;

receiving image data from the first and second imaging arrangements; and combining images captured by the first imaging arrangement and the second imaging arrangement into a single image.

The method may further comprise activating the plurality of light sources sequentially. The method may further comprise combining images captured by the first imaging arrangement and the second imaging arrangement under different illumination conditions into a single image.

Embodiments will now be described, by way of example only, with reference to the accompanying drawings.

BRIEF DESCRIPTION OF THE FIGURES

The figures show:

FIG. 1b shows a perspective view of some detail of the drug delivery device of FIG. 1a;

FIGS. 7a and 7b show a third embodiment of a dose window of the injection device, showing the position of camera lenses, LEDs and resulting reflections.

DETAILED DESCRIPTION

In the following, embodiments will be described with reference to an insulin injection device. The subject matter described herein is however not limited to such application and may equally well be deployed with injection devices that eject other medicaments, or with other types of medical devices.

Figure 1A:
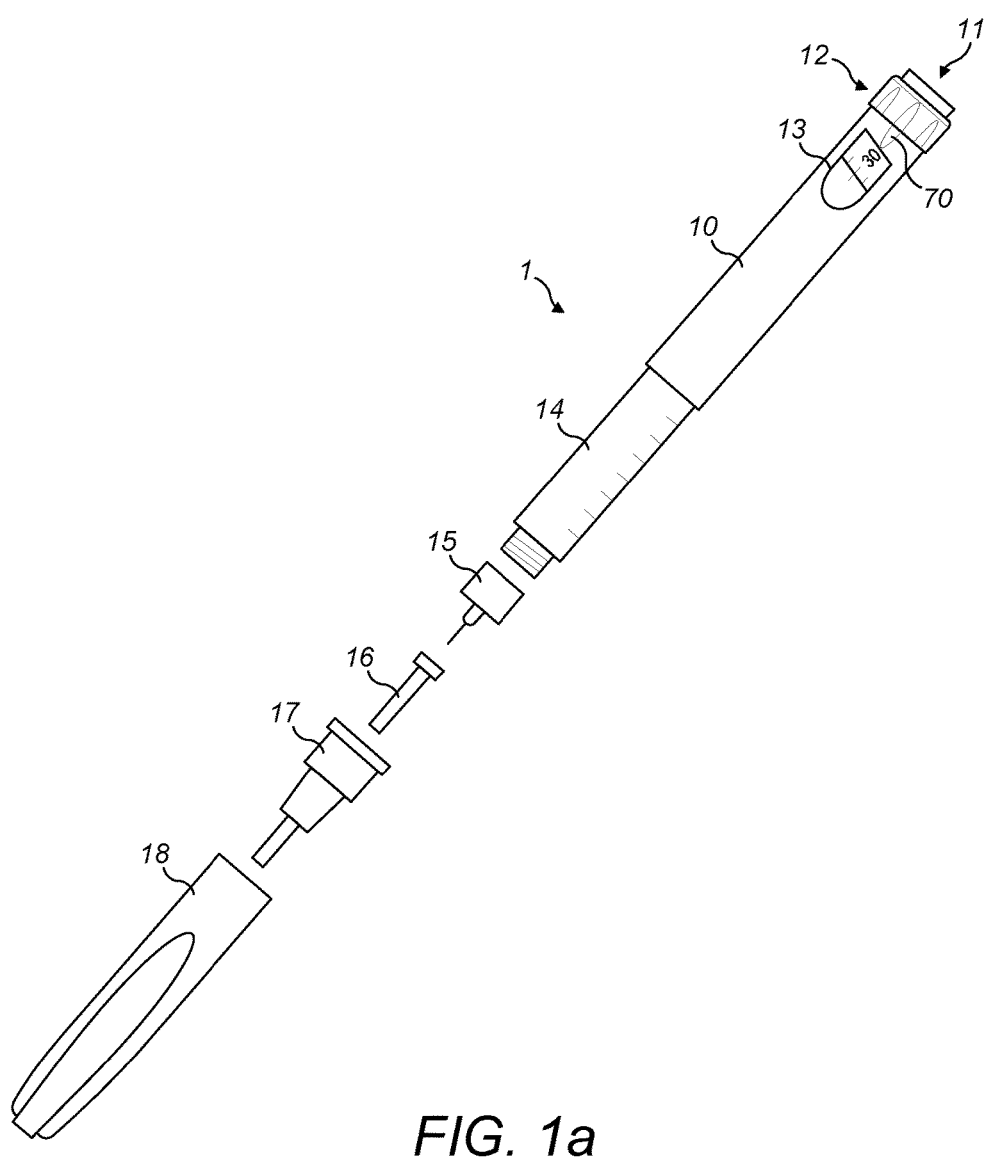
FIG. 1a shows an exploded view of a drug delivery device.

FIG. 1 is an exploded view of an injection device 1 (also referred to herein as a drug delivery device 1, injection pen 1 or pen device 1), which may for instance represent Sanofi's Solostar (R) insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a color. The information identifying the medicament may also be encoded into a barcode, QR code or the like. The information identifying the medicament may also be in the form of a black and white pattern, a color pattern or shading.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
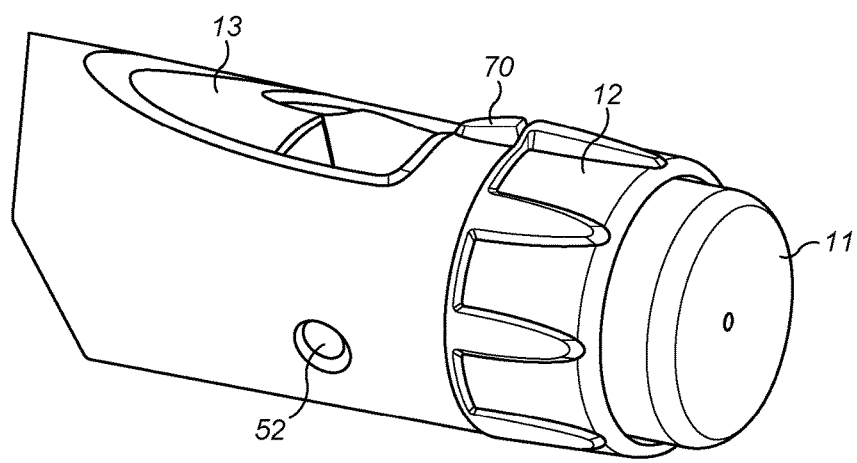

FIG. 1b is a close-up of the end of the injection device 1. This Fig. shows a locating rib 70 that is located between the viewing window 13 and the dosage knob 12.

Figure 2A:
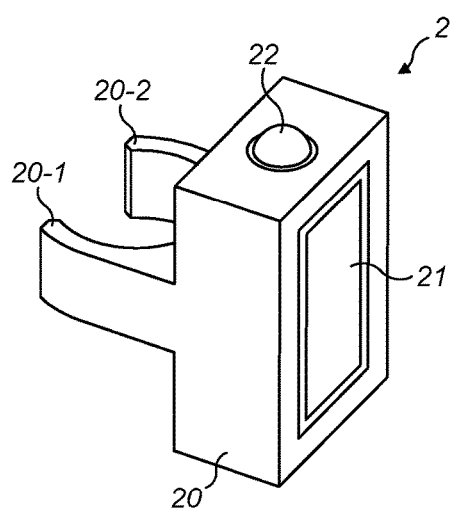
FIG. 2a shows a schematic illustration of a supplementary device to be releasably attached to the drug delivery device of FIGS. 1a and 1b according to an aspect.

FIG. 2a is a schematic illustration of an embodiment of a supplementary device 2 (also referred to herein as an additional device 2, clip-on device 2 or sensor device 2) to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
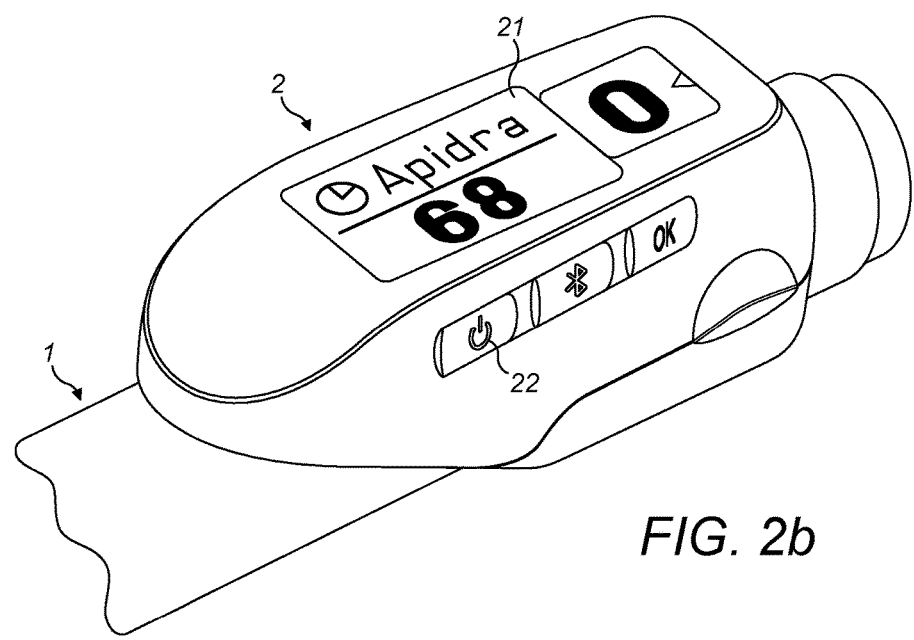
FIG. 2b shows a perspective view of a supplementary device to be releasably attached to the drug delivery device of FIGS. 1a and 1b according to various aspects.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
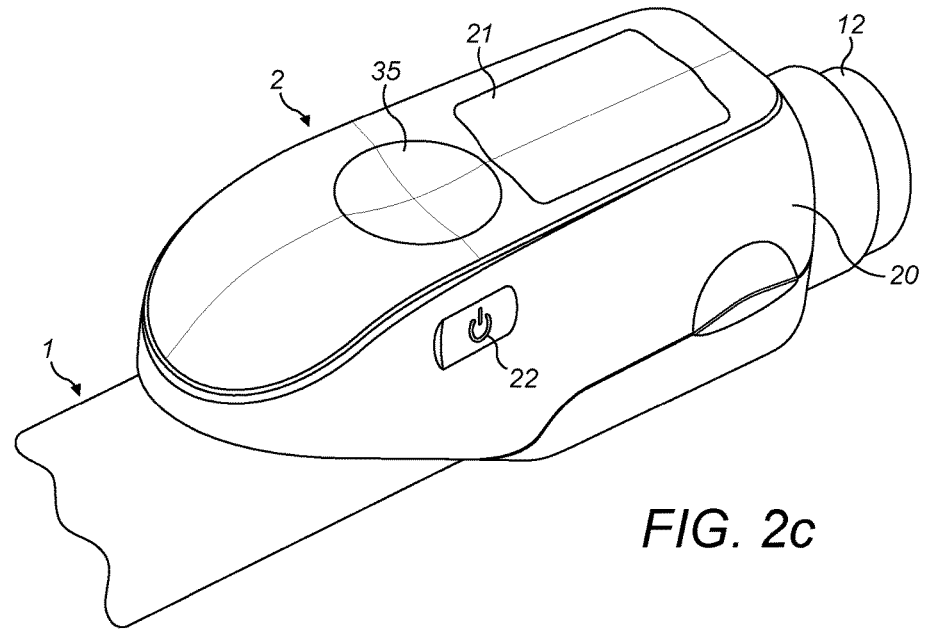
FIG. 2c shows a perspective view of a supplementary device to be releasably attached to the drug delivery device of FIGS. 1a and 1b according to other aspects.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
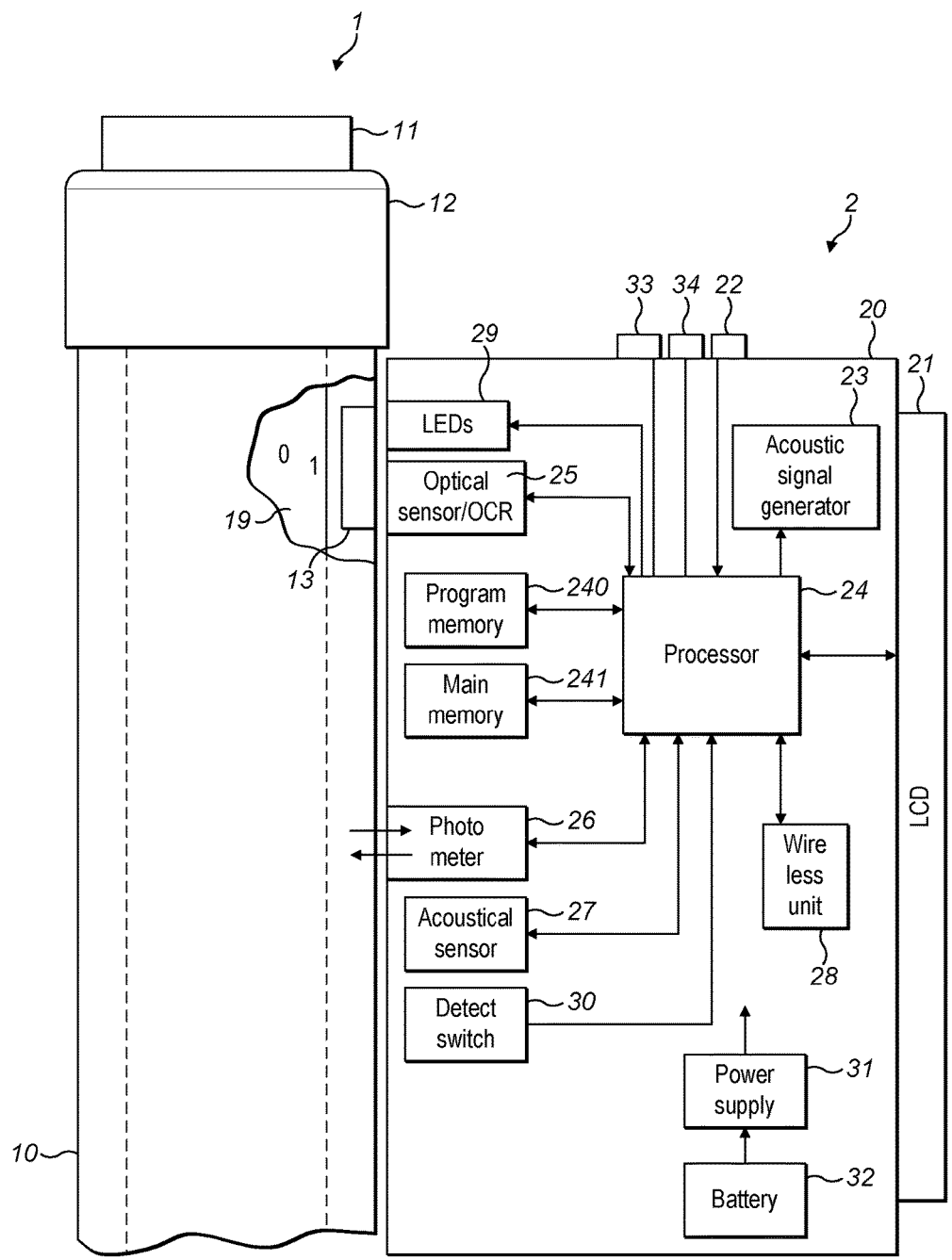
FIG. 3 shows a schematic view of a supplementary device attached to a drug delivery device showing components of the supplementary device.

FIG. 3 shows a schematic view of the supplementary device 2 of FIG. 2a in a state where it is attached to injection device 1 of FIG. 1.

With the housing 20 of supplementary device 2, a plurality of components are contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources (also referred to herein as illumination sources) such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ratio may be 0.13.

Processor 24 further controls a photometer 26, that is configured to determine an optical property of the housing 10 of injection device 1, for example a color or a shading. The optical property may only be present in a specific portion of housing 10, for example a color or color coding of sleeve 19 or of an insulin container comprised within injection device 1, which color or color coding may for instance be visible through a further window in housing 10 (and/or in sleeve 19). Information on this color is then provided to processor 24, which may then determine the type of injection device 1 or the type of insulin contained in injection device 1 (e.g. SoloStar Lantus with purple color and SoloStar Apidra with blue color. Alternatively, a camera unit may be used instead of photometer 26, and an image of the housing, sleeve or insulin container may then be provided to processor 24 to determine the color of the housing, sleeve or insulin container by way of image processing. Further, one or more light sources may be provided to improve reading of photometer 26. The light source may provide light of a certain wavelength or spectrum to improve color detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 4:
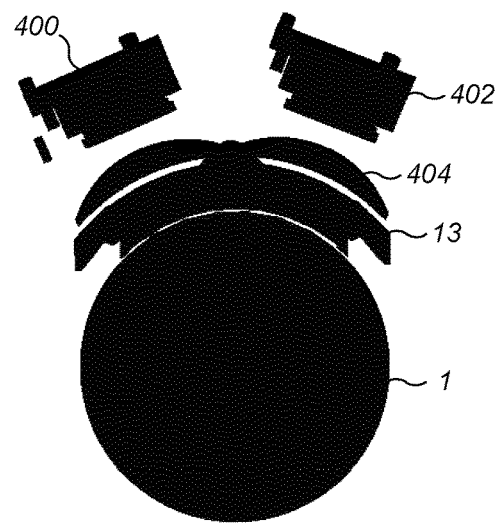
FIG. 4 shows a schematic illustration of the injection device and supplementary device showing reflections from a dose window of the injection device.

FIG. 4 shows schematically a cross-section of the injection device 1 and components of the supplementary device 2. The dose window 13 of the injection device 1 is shown. The supplementary device comprises a first optical sensor 400, a second optical sensor 402 and a plurality of LEDs 29 (not shown). The supplementary device 2 also comprises a protection window 404. The primary function of the protection window 404 is to seal the supplementary device 2 and prevent the ingress of dust and debris. However the protection window 404 may also be shaped as shown in FIG. 4 to provide magnification and/or focussing for the optical sensors 400, 402. Due to manufacturing requirements and costs considerations, the dose window 13 is not usually made of a highly non-reflective material or provided with a non-reflective coating. The dose window may be made of a clear Polycarbonate. Therefore, some of the light incident on the dose window 13 will be reflected from the dose window 13, rather than passing through to be incident on the number sleeve 19. These reflections lead to glare in the images captured by the optical sensors 400, 402. As the LEDs 29 are point light sources, this glare generally takes the form of bright spots. The glare leads to areas of over exposure and impacts the ability of the optical sensors 400, 402 to capture a high quality image of the numbers printed on the number sleeve 19, which in turn affects the ability of the processor 24 to perform a successful optical character recognition process on the numbers. It can be particularly hard to avoid glare in the captured image because the dose window 13 is curved and so the light is incident on the dose window 13 over a range of angles. LEDs 29 are the preferred choice of illumination because of their small size and cost and their radiation characteristics. However, an alternative source, such as a light bulb, diode laser or an organic LED may be used.

Figure 5:
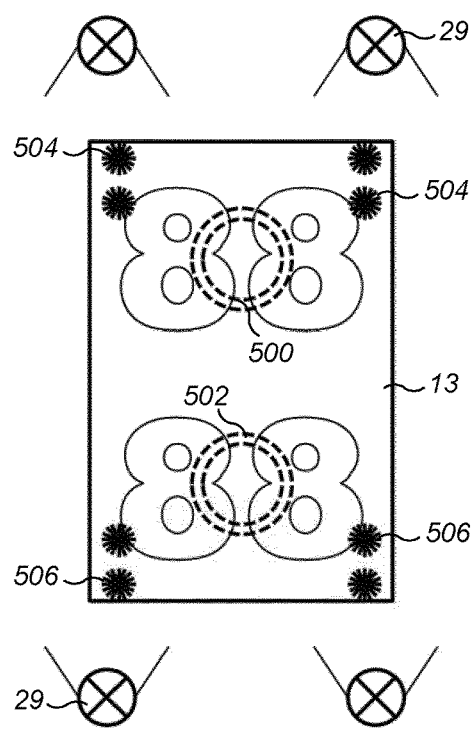
FIG. 5 shows an illustration of a dose window of the injection device, showing the positions of camera lenses, LEDs and resulting reflections.

FIG. 5 shows a first example of the dose window 13 being illuminated by a plurality of LEDs 29. In some embodiments, the field of view of each of the optical sensors 400, 402 is large enough to capture an image of the entire dose window 13. In this embodiment the supplementary device 2 is provided with four LEDs 29 located in pairs above and below the dose window 13. The approximate positions of the first and second optical sensors 400, 402 above the dose window 13 are indicated by first circle 500 and second circle 502. The LEDs 29 located above the dose window 13 lead to upper reflections 504 visible in the field of view of the first optical sensor 400. The LEDs 29 below the dose window 13 lead to lower reflections 506 in the field of view of the second optical sensor 402. The LEDs 29 are positioned such that they produce reflections which are only visible in the field of view of one of the two optical sensors 400, 402. The reflections 504, 506 are also located towards the edge of the dose window 13, away from the main area occupied by the printed numbers.

It should be noted that the number 88 is used in this exemplary embodiment and in other embodiments described herein. In general, this number occupies the greatest amount of space and is therefore the best candidate for assessing whether the reflections from the dose window 13 are located over the numbers. The skilled person will appreciate that the numbers printed on the number sleeve 19 represent a dose of medicament dialed into the injection device 1 and will therefore be sequential. For example, the numbers printed on the number sleeve 19 may be ascending even numbers. In some embodiments the maximum dose which can be dialed into the injection device 1 is 80 units.

In the embodiment illustrated in FIG. 5, the LEDs 29 above and below the dose window 13 are activated simultaneously by the processor 24. The processor 24 then controls both the first optical sensor 400 and the second optical sensor 402 to simultaneously capture images of the number sleeve 19. The processor 24 then employs an imagine processing algorithm to combine the images captured by the first and second optical sensors 400, 402 (image stitching). As each set of reflections occur only towards the edge of the dose window 13, away from the main area occupied by the printed numbers and only in one of the two optical sensors at a time, an overlay of the two images produces a clearer final image.

In some other embodiments, the images captured by the optical sensors 400, 402 may be combined in such a way that the reflections 504, 506 are removed from the final image or significantly reduced in intensity. This may be done by detecting those parts of the captured images which are over exposed and discarding these parts in favor of the same image section from the other of the optical sensors. Alternatively, the processor 24 may be pre-programmed to use the bottom half of the image captured by the first optical sensor 400 and the top half of the image captured by the second optical sensor 402. The processor 24 then passes the final image 514 to an optical character recognition module, or performs the OCR process itself in order to identify the numbers visible in the image. OCR techniques are in general well known, and the skilled person will be aware of a number of OCR methods which could be applied to the subject matter described herein. In some other embodiments, the optical sensors 400, 402 are arranged and/or focussed such that the field of view of each sensor covers only an upper or lower portion of the dose window 13. Once the images are captured, a single final image of the whole dose window 13 is created by joining the two images together.

Figures 6A, 6B:
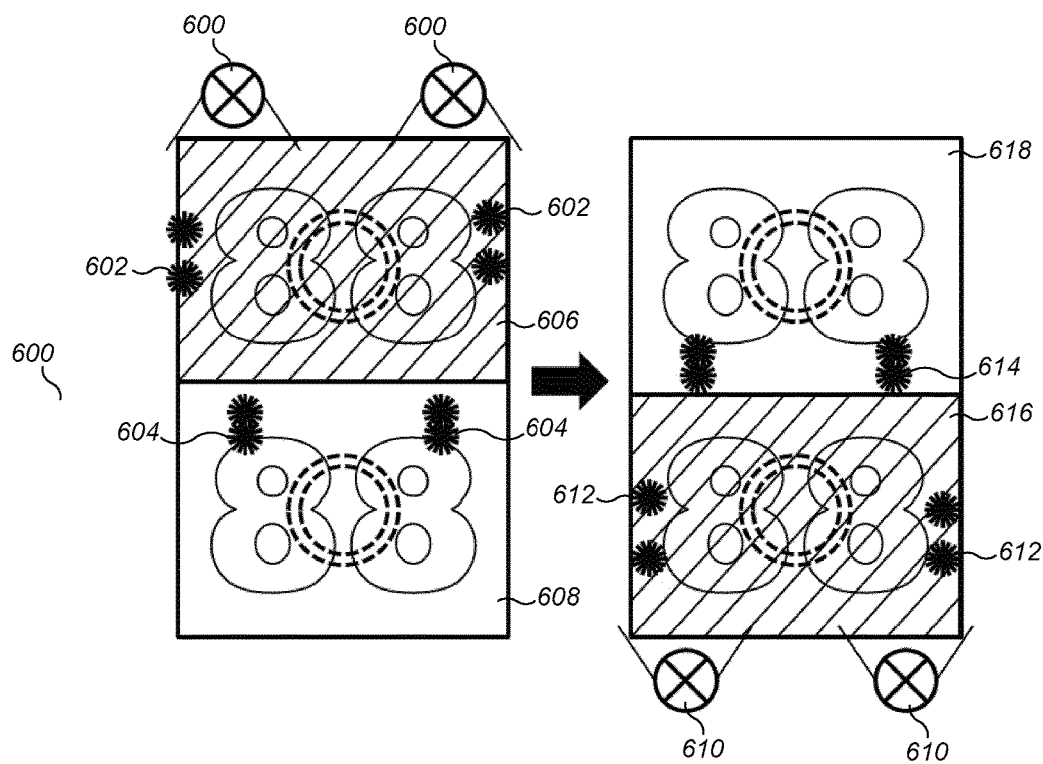
FIGS. 6a and 6b show a second embodiment of a dose window of the injection device, showing the position of camera lenses, LEDs and resulting reflections.

In some embodiments it may not be possible, or may not be desirable, to position the LEDs 29 sufficiently far away from the dose window 13 such that reflections which obscure parts of the numbers do not appear. FIGS. 6a and 6b illustrate a second embodiment in which the LEDs 29 are located closer to the dose window 13 than in the first embodiment. Due to the relative positions of the LEDs 29 and optical sensors 400, 402 each LED 29 produces two reflections from the dose window 13 which are within the field of view of each of the first and second optical sensors 400, 402. In this embodiment the supplementary device 2 again comprises four LEDs 29 arranged in pairs above and below the dose window 13. In this embodiment the first and second optical sensors 400, 402 capture images under different illumination conditions. The processor 24 is configured to divide images captured by the optical sensors 400, 402 into two halves. Processor 24 is configured to control activation and deactivation of the LEDs 29 and to control the image capture process of each of the optical sensors 400, 402.

The processor 24 first activates the upper LEDs 600 which causes upper reflections 602 to appear in the field of view of the first optical sensor 400 and lower reflections 604 to appear in the field of view of the second optical sensor 402. Due to the position of the upper LEDs 600 relative to the dose window 13 and the two optical sensors 400, 402, the upper reflections 602 appear at the periphery of the dose window 13, away from the area of the numbers. The lower reflections 604, visible to the second optical sensor 402, appear more centrally and may overlap with the area of the numbers. The processor 24 therefore controls the first optical sensor 400 to capture an image of the number sleeve 19 when the upper LEDs 600 are activated. The first optical sensor 400 may capture an image of the whole of the dose window 13, in which case the processor 24 keeps the upper half 606 of this image and discards the lower half 608 of the image. Alternatively, the first optical 400 may be orientated and focused in such a way that it captures an image of only the upper half 606 of the dose window 13.

The next step is illustrated in FIG. 6b in which the processor 24 deactivates the upper LEDs 600 and activates the lower LEDs 610. The lower LEDs 610 produce lower reflections 612 in the field of view of the second optical sensor 402. These lower reflections 612 are located at the periphery of the field of view of the second optical sensor 402, away from the area of the numbers. The lower LEDs 610 also produce upper reflections 614 in the field of view of the first optical sensor 400. The upper reflections 614 are located more centrally within the field of view of the first optical sensor 400 and may overlap with the area of the numbers. The processor 24 therefore controls the second optical sensor 402 to capture an image of the dose window 13 while the lower LEDs 610 are activated. The second optical sensor 402 may capture an image of the whole dose window 13, in which case the processor 24 is configured to keep the lower half 614 of this image and discard the upper half 618 of the image. Alternatively, the second optical sensor 402 may be orientated and focussed in such a way that it captures an image of only the lower half 614 of the dose window 13.

Once the processor 24 has controlled the first and second optical sensors 400, 402 to capture images of the dose window 13 under different illumination conditions, the two images are combined together to create a final image. In practice, the image halves captured in the first and second images may overlap. This may be done to ensure that no image information is lost. The processor 24 may execute software which uses edge detection techniques to determine the appropriate place in each image for the combination to occur. The processor 24 then passes the final image to an optical character recognition module, or performs the OCR process itself in order to identify the numbers visible in the image.

Positioning the LEDs 29 closer to the dose window 13 improves the illumination of the number sleeve 19 and increases the amount of light reaching the dose window 13 and optical sensors 400, 402 for a given LED light output. Having two optical sensors 400, 402 positioned above respective halves of the dose window 13, rather than a single centrally located optical sensor results in the reflections in each sensor's field of view being located at the periphery of the image, away from the area of the numbers. In general, it is desirable to position the LEDs 29 such that minimal reflections appear in the illuminated area, while at the same time producing an illumination which is bright and homogeneous. Thus the LEDs 29 are positioned such that the reflections produced appear in a section of the field of view and captured image which is subsequently discarded. Another advantage of the subject matter described herein is that it requires no modification of existing injection pen designs to implement.

In some embodiments only even numbers are printed, in ascending order, on the number sleeve 19. In this case the arrangements shown in FIGS. 5 to 6b represent a situation in which an odd number of units is dialed into the injection device 1. This is because the number of dialed units would normally be displayed centrally within the dose window 13.

FIGS. 7a and 7b illustrate a situation which only even numbers are printed on the number sleeve 19 and where a dose of 26 units has been dialed into the injection device 1. Thus the number 26 is centrally in the dose window 13. The position of the LEDs 29 in FIGS. 7a and 7b is the same as in FIGS. 6a and 6b, with a pair of LEDs 29 located at either end of the dose window 13. This arrangement of LEDs 29 therefore leads to the same pattern of reflections in the fields of view of the optical sensors 400, 402. It can be seen that the reflections produced by the LEDs 29 may overlap with the area of the numbers to a greater extent when the number is located in the centre of the dose window 13. However, the processor 24 may perform the same over-exposure detection and removal process using the two images captured by the first and second optical sensors 400, 402. Alternatively, the processor 24 may still divide the field of view of each of the optical sensors 400, 402 into upper and lower halves, or the sensors may be orientated and focused onto one half of the dose window 13. Alternatively, the LEDs may be activated in left and right pairs and the processor 24 may divide the field of view of each of the optical sensors 400, 402 into left and right halves. The combination of the two images in this situation needs to be accurate as the joining point between the images passes through the number of interest. The processor 24 may additionally be configured to detect the white spaces between the printed numbers in order to determine whether a number is displayed centrally within the dose window 13 or not.

The invention claimed is:

1. A supplementary device for attachment to an injection device, the supplementary device comprising:
   a first imaging arrangement and a second imaging arrangement each configured to capture an image of a moveable number sleeve of the injection device from different respective angles;
   a plurality of light sources; and
   a processor arrangement configured to control operation of the first imaging arrangement and the second imaging arrangement and the plurality of light sources and to receive image data from each of the imaging arrangements,
   wherein the processor arrangement is configured to combine images captured by the first imaging arrangement and the second imaging arrangement into a single image.

2. A supplementary device according to claim 1, wherein the processor arrangement is further configured to activate the plurality of light sources sequentially and to combine images captured by the first imaging arrangement and the second imaging arrangement under different illumination conditions into a single image.

3. A supplementary device according to claim 1, wherein the processor arrangement is configured to activate all of the plurality of light sources simultaneously.

4. A supplementary device according to claim 1, wherein the processor is configured to divide a field of view of each of the first imaging arrangement and the second imaging arrangement into a plurality of areas and to associate each of the areas with a respective illumination condition.

5. A supplementary device according to claim 4, wherein the processor arrangement is configured to combine multiple images captured by the first imaging arrangement and the second imaging arrangement into a single image by being configured to combine an image of a first area of the plurality of areas captured by the first imaging arrangement under a first illumination condition with an image of a second area of the plurality of areas captured by the second imaging arrangement under a second illumination condition.

6. A supplementary device according to claim 1, wherein the supplementary device comprises four light sources grouped into a first pair of light sources and a second pair of light sources and wherein the processor arrangement is configured to activate the plurality of light sources sequentially by being configured to activate the first pair of light sources followed by the second pair of light sources.

7. A supplementary device according to claim 6, wherein the processor is configured to:
   control the first imaging arrangement to capture a first image of the moveable number sleeve when the first pair of light sources are activated; and
   control the second imaging arrangement to capture a second image of the moveable number sleeve when the second pair of light sources are activated.

8. A supplementary device according to claim 7, wherein the processor is configured to divide a field of view of the first imaging arrangement and a field of view of the second imaging arrangement into first and second halves.

9. A supplementary device according to claim 8, wherein the processor is configured to keep the first half of the first image and discard the second half of the first image and to keep the second half of the second image and discard the first half of the second image.

10. A supplementary device according to claim 9, wherein the processor arrangement is configured to combine images captured by the first imaging arrangement and the second imaging arrangement into a single image by being configured to combine the first half of the first image and the second half of the second image into a single image.

11. A supplementary device according to claim 1, wherein each of the plurality of light sources, when activated, results in one or more reflections from a transparent window of the injection device being visible in a field of view of each of the first imaging arrangement and the second imaging arrangement.

12. A system comprising a supplementary device according to claim 1 and the injection device comprising the moveable number sleeve and being configured to have the supplementary device attached thereto.

13. A method of operating a supplementary device for attachment to an injection device, the supplementary device having a first imaging arrangement and a second imaging arrangement each configured to capture an image of a moveable number sleeve of the injection device from different respective angles, a plurality of light sources and a processor arrangement, the method comprising:
   controlling operation of the first imaging arrangement, the second imaging arrangement and the plurality of light sources;
   receiving image data from the first imaging arrangement and the second imaging arrangements; and
   combining images captured by the first imaging arrangement and the second imaging arrangement into a single image.

14. A method of operating a supplementary device according to claim 13, the method further comprising activating the plurality of light sources sequentially.

15. A method of operating a supplementary device according to claim 14, the method further comprising combining images captured by the first imaging arrangement and the second imaging arrangement under different illumination conditions into a single image.

* * * * *